(12) United States Patent
Brunel et al.

(10) Patent No.: US 10,729,701 B2
(45) Date of Patent: Aug. 4, 2020

(54) COMPOUNDS THAT ARE ANALOGS OF SQUALAMINE, USED AS ANTIBACTERIAL AGENTS

(71) Applicant: VIRBAC, Carros (FR)

(72) Inventors: Jean-Michel Brunel, Marseilles (FR); Jean-Pascal Marc, Saint Paul de Vence (FR)

(73) Assignee: VIRBAC, Carros (FR)

( * ) Notice: Subject to any disclaimer, the term of this patent is extended or adjusted under 35 U.S.C. 154(b) by 0 days.

(21) Appl. No.: 15/555,596

(22) PCT Filed: Mar. 11, 2016

(86) PCT No.: PCT/IB2016/051408
§ 371 (c)(1),
(2) Date: Sep. 5, 2017

(87) PCT Pub. No.: WO2016/142922
PCT Pub. Date: Sep. 15, 2016

(65) Prior Publication Data
US 2018/0042942 A1 Feb. 15, 2018

(30) Foreign Application Priority Data

Mar. 12, 2015 (FR) .................................... 15 52048

(51) Int. Cl.
| *A61K 31/58* | (2006.01) |
| *A61K 31/575* | (2006.01) |
| *A61K 45/06* | (2006.01) |
| *C07J 41/00* | (2006.01) |
| *C07J 43/00* | (2006.01) |

(52) U.S. Cl.
CPC ............ *A61K 31/575* (2013.01); *A61K 31/58* (2013.01); *A61K 45/06* (2013.01); *C07J 41/0005* (2013.01); *C07J 43/003* (2013.01)

(58) Field of Classification Search
CPC ...... A61K 31/58; A61K 31/575; A61K 45/06; C07J 41/00; C07J 43/00
See application file for complete search history.

(56) References Cited

U.S. PATENT DOCUMENTS 5,763,430 A * 6/1998 Zasloff ................. C07J 41/0005
514/169
9,365,608 B2 * 6/2016 McLane ..................... C07J 5/00

FOREIGN PATENT DOCUMENTS

| WO | 96/40728 A2 | 12/1996 |
| WO | 2009/032321 A2 | 3/2009 |
| WO | 2011/067501 A1 | 6/2011 |
| WO | 2013/104849 A1 | 7/2013 |

OTHER PUBLICATIONS

Carbone et al., PNAS, Nov. 20, 2012, vol. 109, No. 47, pp. 19226-19231.*
International Search Report issued in corresponding International Application No. PCT/IB2016/051408 dated May 9, 2016.
Walker et al., "Squalamine and its derivatives as potential antitubercular compounds," Tuberculosis, 93: 102-103 (2013).

* cited by examiner

*Primary Examiner* — Sun Jae Yoo
(74) *Attorney, Agent, or Firm* — Morgan, Lewis & Bockius LLP

(57) ABSTRACT

The invention relates to compounds of formula (I), to the pharmaceutical compositions comprising same, and to the use thereof in the treatment of bacterial, fungal, viral and parasitic infections or in the treatment of cancer in humans or animals. In formula (I), R1 and R2 are as defined in claim 1.

13 Claims, No Drawings

COMPOUNDS THAT ARE ANALOGS OF SQUALAMINE, USED AS ANTIBACTERIAL AGENTS

The invention relates to squalamine analogs for their use in the treatment of bacterial, fungal, viral or parasitic infections or in the treatment of cancer in man or animals, and also to the pharmaceutical or veterinary compositions comprising them.

In 1993, squalamine, a natural steroid, isolated mainly from the tissues of a small shark *Squalus acanthias,* proved to be a very active substance exhibiting essentially an antiangiogenic activity against cells and an antiviral and antibacterial activity.

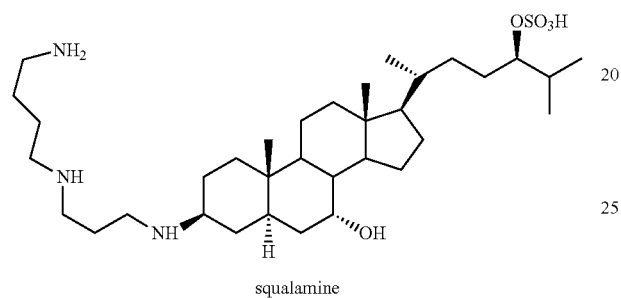

squalamine

Chemically, squalamine is a novel molecule exhibiting an amphiphilic nature. It thus comprises a nonpolar central part (a backbone of cholestane type) and two polar ends (a polyamine chain and a sulfate group).

Initially, this water-soluble polyaminosterol had aroused interest for its antiangiogenic and antimicrobial properties with regard to a variety of Gram positive bacteria (*Staphylococcus aureus, Enterococcus faecalis*), Gram-negative bacteria (*Escherichia coli, Pseudomonas aeruginosa*), fungi (*Candia albicans, Candida tropicalis*) and protozoa.

As the natural source of squalamine is limited, aminosteroidal analogous synthetic derivatives of squalamine have been looked for. Derivatives or analogs comprising a polyamine chain in the 3 or 7 position of 10, 13-dimethyl-17-octyl cholestane or cholestene rings, optionally hydroxylated in the 7 or respectively 3 position, have been described in particular. Derivatives of formula IIa, IIb, IIc, IId and II-1 below have in particular been described as exhibiting an antibacterial activity similar to squalamine with regard to various multiresistant Gram-positive and Gram-negative bacteria (WO 2011/067501 and references 1 to 7).

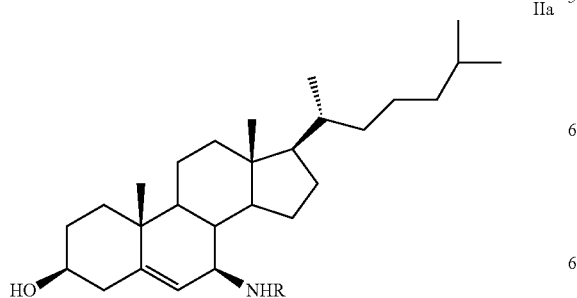

IIa

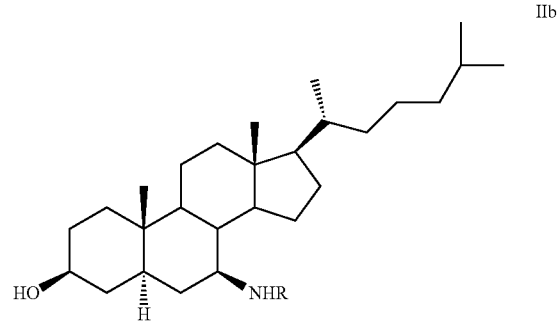

IIb

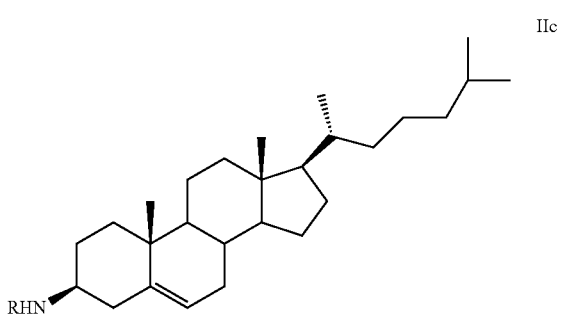

IIc

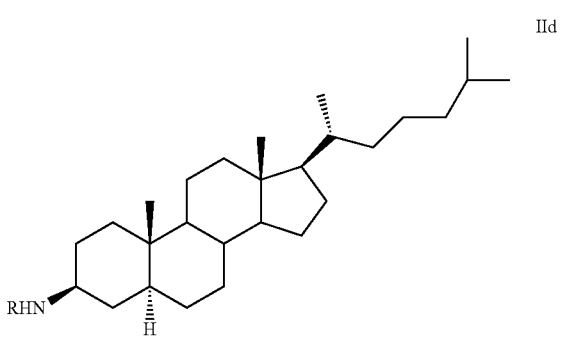

IId

An application of these derivatives in a curative treatment of pulmonary infections by the aerosol route has more particularly been suggested. However, the applicant company has observed that these compounds exhibit a high cytotoxicity and that the compounds of formulae IIc and IId exhibit a low activity against certain Gram-negative bacteria, such as *E. coli.*

Compounds analogous to squalamine have now been discovered which exhibit a good antibacterial activity against Gram-positive and Gram-negative bacteria, while advantageously being less cytotoxic than squalamine.

Thus, according to a first subject matter, the invention relates to a compound of formula (I):

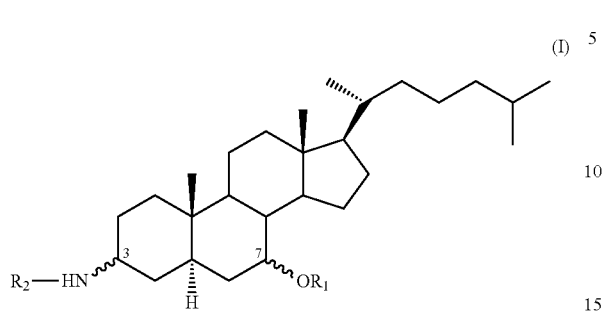

(I)

in which:

$R_1$ is chosen from H, $SO_3H$, a $C_1$-$C_8$ alkyl group, a $C_6$-$C_{10}$ aryl group or a $C(=O)R_{11}$ group, $R_2$ is $—(CR_3R_4)_m—(X)_p—(CR_5R_6)_n—[(Y)—(CR_7R_8)_o]_q—NR_9R_{10}$, $R_3$, $R_4$, $R_5$, $R_6$, $R_7$ and $R_8$ are, in each case, identical or different, each independently chosen from H, $C_1$-$C_8$ alkyl, $C_6$-$C_{10}$ aryl and $C(=O)OR_{12}$;

$R_9$ and $R_{10}$, which are identical or different, are each independently chosen from H, $C_1$-$C_8$ alkyl or a $—(CH_2)_r—NH_2$ group or together form a 5- to 7-membered heterocyclyl group optionally substituted by one to three $R_{14}$ groups;

X and Y, which are identical or different, are in each case each independently chosen from $NR_{13}$, O or a 5- to 6-membered nitrogenous heterocyclyl group, $R_{11}$ and $R_{12}$ are each independently chosen from a $C_1$-$C_8$ alkyl group or a $C_6$-$C_{10}$ aryl group, $R_{13}$ is H, a $C_1$-$C_6$ alkyl group or a $—(CH_2)_s—NH_2$ group;

$R_{14}$ is a $=O$ or $=S$ group;

m is an integer between 1 and 5;

n is an integer between 1 and 5, o is an integer between 1 and 5, p is 0 or 1, q is 0, 1 or 2, r is an integer between 1 and 4, s is an integer between 1 and 5;

it being understood that, when p=1 and q=1, then m+n+o≠7, and also to the stereoisomers, mixtures of stereoisomers and/or pharmaceutically acceptable salts of these, for their use in the treatment of bacterial, fungal, viral or parasitic infections or in the treatment of cancer in man or animals.

The invention also relates to a compound of formula (I):

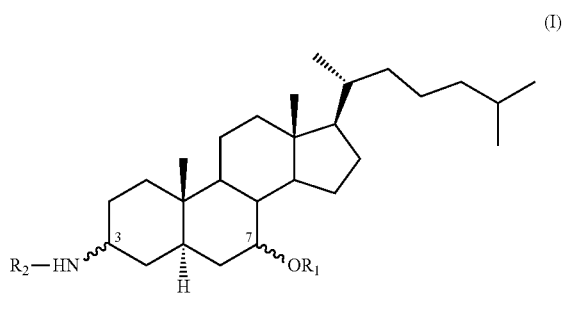

(I)

in which:

$R_1$ is chosen from H, $SO_3H$, a $C_1$-$C_8$ alkyl group, a $C_6$-$C_{10}$ aryl group or a $C(=O)R_{11}$ group, $R_2$ is $—(CR_3R_4)_m—(X)_p—(CR_5R_6)_n—[(Y)—(CR_7R_8)_o]_q—NR_9R_{10}$, $R_3$, $R_4$, $R_5$, $R_6$, $R_7$ and $R_8$ are, in each case, identical or different, each independently chosen from H, $C_1$-$C_8$ alkyl, $C_6$-$C_{10}$ aryl and $C(=O)OR_{12}$;

$R_9$ and $R_{10}$, which are identical or different, are each independently chosen from H, $C_1$-$C_8$ alkyl or a $—(CH_2)_r—NH_2$ group or together form a 5- to 7-membered heterocyclyl group optionally substituted by one to three $R_{14}$ groups;

X and Y, which are identical or different, are in each case each independently chosen from $NR_{13}$, O or a 5- to 6-membered nitrogenous heterocyclyl group, $R_{11}$ and $R_{12}$ are each independently chosen from a $C_1$-$C_8$ alkyl group or a $C_6$-$C_{10}$ aryl group, $R_{13}$ is H, a $C_1$-$C_6$ alkyl group or a $—(CH_2)_s—NH_2$ group;

$R_{14}$ is a $=O$ or $=S$ group;

m is an integer between 1 and 5;

n is an integer between 1 and 5, o is an integer between 1 and 5, p is 0 or 1, q is 0, 1 or 2, r is an integer between 1 and 4, s is an integer between 1 and 5;

and also to the stereoisomers, mixtures of stereoisomers and/or pharmaceutically acceptable salts of these, for their use in the treatment of bacterial, fungal, viral or parasitic infections or in the treatment of cancer in man or animals.

According to a preferred aspect, the compound 3β-(norspermino)-7α-hydroxy-5α-cholestane and the compounds of following formulae are excluded:

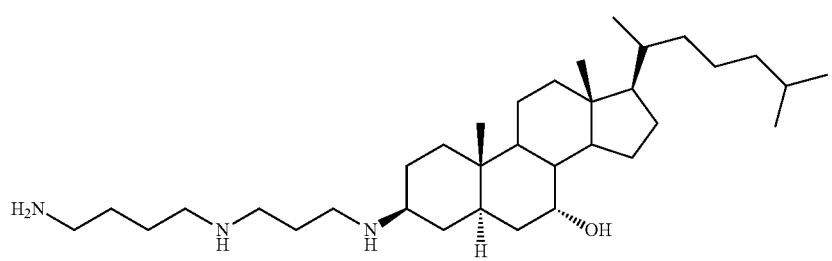

SA-Y

SA-Z

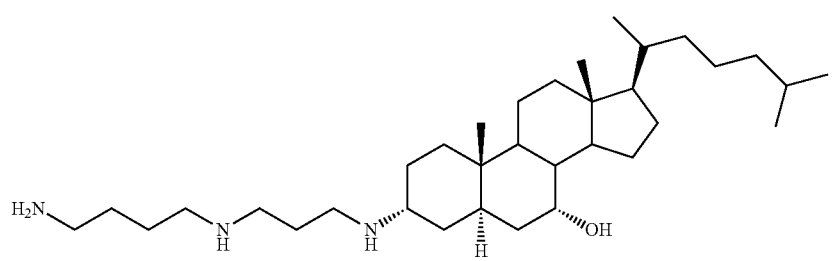

According to a preferred aspect, the compounds for which p=1, q=0, m=3, n=3 or 4, and X=NH are excluded.

According to a preferred aspect, it is understood that:
when p=1 and q=0, then m+n≠6 and 7,
when p=0 and q=1, then m+n+o≠6 and 7.
Preferably, $R_1$ is H.
Preferably, X is $NR_{13}$, more preferably NH.
Preferably, $R_9$ and/or $R_{10}$ are H.
Preferably, m is 2, 3, 4 or 5, more preferably 3.
Preferably, n is 2, 3, 4 or 5, more preferably 2 or 4.

According to a preferred aspect, the invention includes compounds of formula (I) in which the —$NHR_2$ group is chosen from:

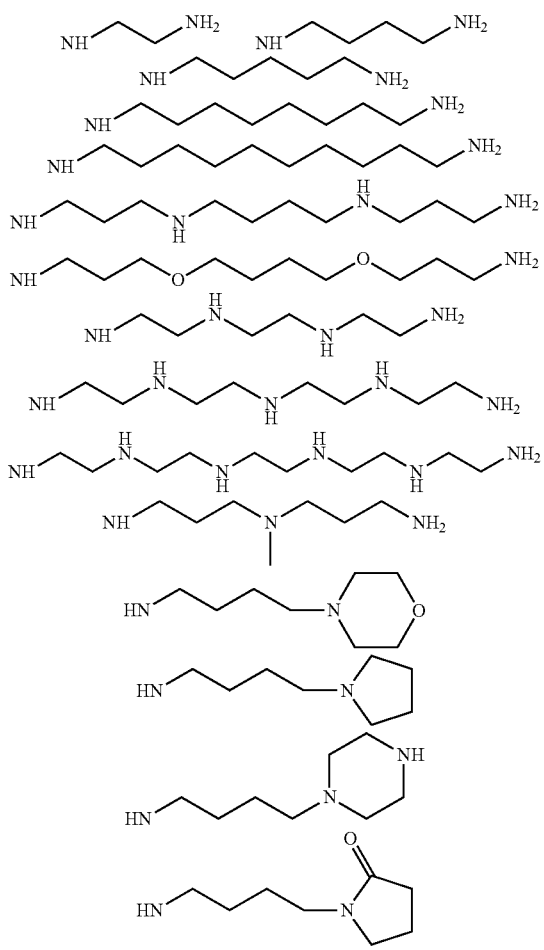

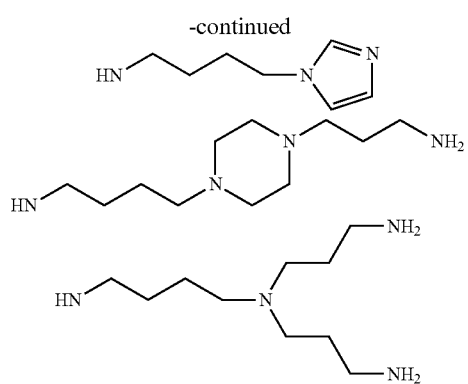

According to a preferred aspect, the invention includes compounds of formula (I) in which the —$NHR_2$ group is chosen from:

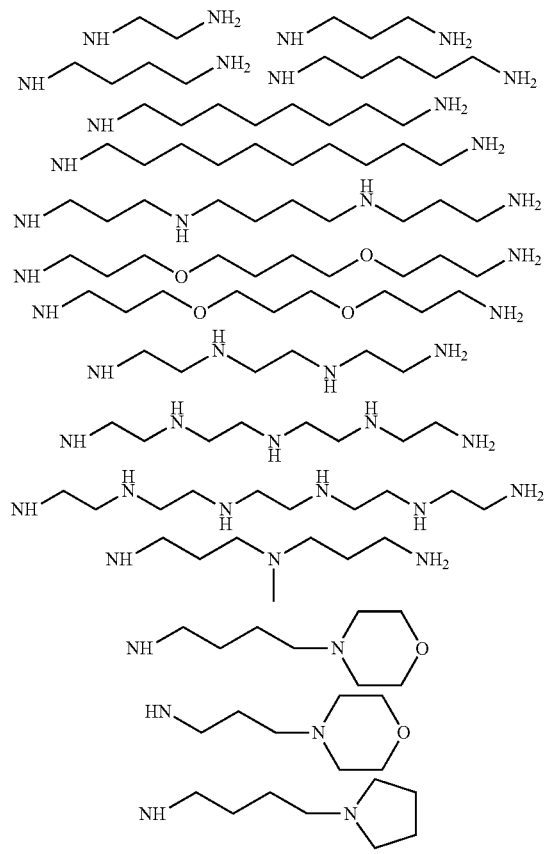

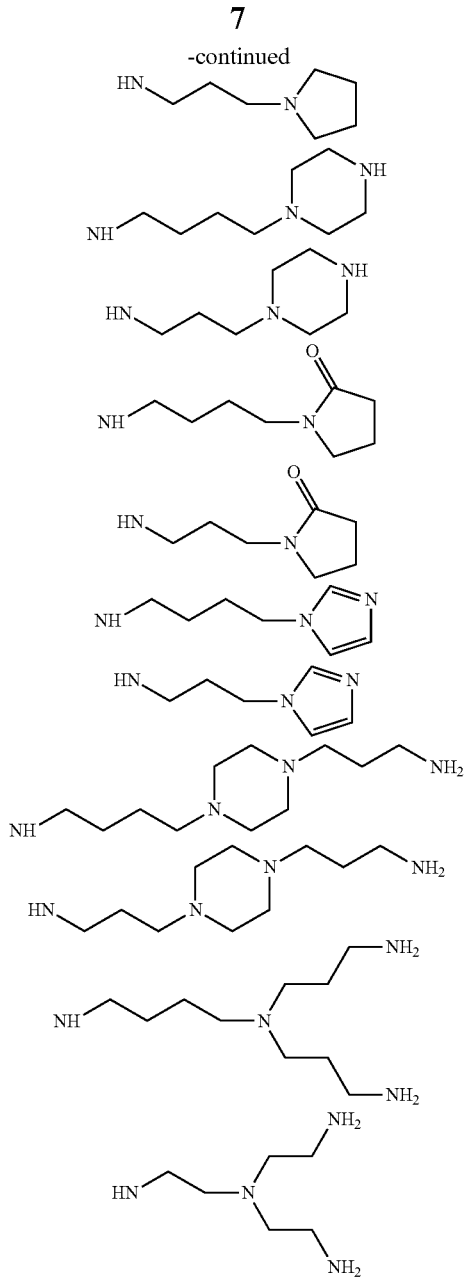

According to a preferred alternative form, the compounds of formula (I) are chosen from:
3β-spermino-7α-hydroxy-5α-cholestane (SA-1)
3β-spermino-7β-hydroxy-5α-cholestane (SA-2)
3β-norspermidino-7β-hydroxy-5α-cholestane (SA-3)
3β-(1,3-diaminopropane)-7β-hydroxy-5α-cholestane (SA-4)
3β-(1,4-diaminobutane)-7β-hydroxy-5α-cholestane (SA-5)
3β-(tris(2-aminoethyl)amine)-7β-hydroxy-5α-cholestane (SA-6)
3β-(1,5-diaminopentane)-7α-hydroxy-5α-cholestane (SA-7)
3β-(1,4-bis(3-aminopropyl)piperazine)-7β-hydroxy-5α-cholestane (SA-8)
3β-(1,4-bis(3-aminopropoxy)butane)-7β-hydroxy-5α-cholestane (SA-9)
3β-(norspermino)-7α-hydroxy-5α-cholestane (SA-10)
3β-(1-(3-aminopropyl)imidazole)-7α-hydroxy-5α-cholestane (SA-11)
3β-(1-(3-aminopropyl)morpholine)-7α-hydroxy-5α-cholestane (SA-12)

According to another preferred alternative form, the compounds of formula (I) are chosen from:
3β-spermino-7β-hydroxy-5α-cholestane (SA-2)
3β-(1,3-diaminopropane)-7β-hydroxy-5α-cholestane (SA-4)
3β-(norspermino)-7α-hydroxy-5α-cholestane (SA-10)

According to another preferred alternative form, the invention includes compounds of formula (I) for the treatment of bacterial infections, in particular Gram-positive bacterial infections, such as *Staphylococcus aureus, Staphylococcus faecalis* infections, and/or Gram-negative bacterial infections, such as *Escherichia Coli* or *Pseudomonas aeruginosa*.

The compounds of formula (I) according to the invention are of use in particular in the antibiotic treatment of bacterial infections, in particular of strains of Gram-positive or Gram-negative bacteria, in man or in animals. According to one embodiment, the compounds of formula (I) are used in animals, in particular in dogs, cats or ruminants.

By way of example, the compounds according to the invention are of use in the treatment of mastitis, metritis, dental infections, pyodermatitis or otitis, in particular in animals. The compounds according to the invention are also of use in the manufacture of products intended to destroy biofilms.

According to a specific embodiment, the invention relates to the compound SA-10, SA-Y or SA-Z for its use in the treatment of mastitis, metritis, dental infections, pyodermatitis or otitis, in particular in animals. The compound SA-10, SA-Y or SA-Z according to the invention is also of use in the manufacture of products intended to destroy biofilms.

Mastitis is the inflammation of the udder in mammals; it is a common infection in the husbandry of milch females (cows, ewes, she-goats, female buffalos and female camels). It is characterized by the presence, in the milk, of inflammatory cells (leukocytes) and possibly bacteria. This inflammation may have clinical consequences with modification of the appearance of the milk, visible inflammation of the udder (swelling, pain, edema) and possibly attack of the general state. Generally, the disease remains subclinical with detrimental change in the composition of the milk and decrease in production. Mastitis results from an infection of the udder by bacteria more or less adapted to this biotope. In specialized dairy farming, mastitis causes major economic losses (milk not produced, unsuitable for use, detrimental change in the quality of the milk) and constitutes a public health risk (pathogenic bacteria and residual antibiotics). Mastitis is due to the penetration into and then the growth in the mammary gland of a bacterium. The microorganism generally enters through the end of the teat. Mastitis thus generally does not concern all the areas of the udder of the animal. The main bacteria responsible for mastitis can be combined together into two groups, depending on their reservoir of contamination: the microorganisms occurring at the surface of the udder: *Staphylococci, Streptococcus agalactiae, Streptococcus disgalactiae, Streptococcus uberis*. These bacteria are mainly responsible for subclinical mastitis (not detectable with the naked eye), which is sometimes difficult to cure during lactation; the dry period is then taken advantage of to treat the areas infected with the antibiotics. The microorganisms occurring in the environment (bedding): for example, *Streptococcus uberis, Escherichia coli*. These bacteria generally result in clinical mastitis, which can extend as far as the rapid death of the animal in the absence of appropriate treatment. Mycoplasma mastitis still presents problems in goat herds, even if it has currently virtually disappeared appear from cattle herds.

Metritis is an inflammation of the whole of the uterinal wall. It is caused by a bacterial infection and it is virtually always observed after an abnormal parturition or a major uterine infection. Its seriousness ranges from a subclinical infection to an established disease with fever and decrease in milk production. Metritis may predispose cows to ketosis, to displacement of the abomasum and to other postpartum disorders. It can also result in a fall in the fertility, temporary or permanent, and even, in some cases, to the death of the animal. Metritis is often related to contamination of the uterus by the bacterium *Arcanobacterium pyogenes,* either alone or in conjunction with other pathogenic microorganisms, such as: *Fusobacterium necrophorum, Bacteroides* spp. or *Escherichia coli*. Immediately after calving, the uterus constitutes an ideal environment for bacterial growth. During the first postpartum week, up to 90% of cows are victims of a uterine infection of bacterial origin.

Pyodermatitis is a purulent skin disease which may be acute or chronic and local or diffuse. Pyodermatitis is etymologically an infection of the skin. It is of external origin, caused by a bacterium, generally *staphylococcus* or *Streptococcus pyogenes*. A pyodermatitis can be circumscribed or generalized. In dogs, pyotraumatic dermatitis is often observed. It is a skin lesion resulting from a compulsion to scratch, nibble at and lick part of the body. As soon as the lesion is big enough, secondary infection by opportunist bacteria may occur, leading the animal to further nibble or scratch itself. The majority of the animals often affected have allergies: particularly animals allergic to fleas. However, any skin irritation may bring about pyotraumatic dermatitis.

Otitis is an inflammation of the auditory canal. It is an extremely frequent pathology in domestic carnivores, in particular dogs. It can have numerous causes, some which will be responsible for recurrent otitis. Several types of bacteria (*Staphylococci, Pseudomonas,* and the like) and yeasts (*Malassezia*) can grow in the auditory canal, resulting in the appearance of otitis. These types of otitis are then associated with purulent secretions and with a very unpleasant odor.

Periodontal disease or dental infection is the main cause of dental disease in dogs. In spite of being characterized by bad breath, it is often not identified by the owner. Its prevention involves regular care as it can result in the loss of the teeth, indeed even in serious infections. The presence of bacteria in the mouth is normal but, when they grow too rapidly, they can result in the formation of dental plaque. If the plaque accumulates and is not removed, gingivitis (inflammation of the gums) may appear. At this stage, the treatment may be completely curative. However, in the absence of treatment, the disease develops into periodontitis, characterized by a greater inflammation of the gums, deposits of tartar on the teeth and the disappearance of the bone and of the supporting structures surrounding the tooth. The attack can be taken care of but is irreversible. Periodontitis can result in the loss of the teeth and the propagation of serious infections in the liver, heart or lungs.

According to a specific aspect of the invention, the compounds of formula (I) are administered in combination with another antibiotic compound, in particular of the family of the β-lactamines (penicillin/cephalosporins), aminosides, macrolides, polypeptides, sulfamides, quinolones, nitroimidazoles, nitrofuran derivatives, derivatives of the benzylpyrimidine nucleus, tetracyclines or phenicols, such as doxycycline or chloramphenicol, penicillin, ampicillin, amoxicillin, cloxacillin, dicloxacillin, oxacillin, nafcillin, cefalexin, cefapirin, cefazolin, ceftiofur, cefoperazone, cefovecin, cefquinome, thiamphenicol, florfenicol, terramycin, erythromycin, spiramycin, tylosin, josamycin, tilmicosin, tulathromycin, gamithromycin, tildipirosin, clindamycin, lincomycin, pirlimycin, tiamulin, valnemulin, oxolinic acid, flumequine, enrofloxacin, danofloxacin, ibafloxacin, marbofloxacin, difloxacin, orbifloxacin, pradofloxacin, rifampicin, rifaximin, sulfamethizole, sulfathiazole, sulfadimidine, sulfamethoxazole, sulfadiazine, sulfadimethoxine, sulfamethoxypyridazine, trimethoprim, baquiloprim, metronidazole, dimetridazole, ronidazole, nitrofurantoin, furazolidone or furaltadone. In a particularly advantageous use of the compounds of the invention, a synergy is observed during the joint use of the compounds of the invention with antibiotics. This is because it has been observed that, when the compounds of formula (I) were combined with another antibiotic compound, for example doxycycline or chloramphenicol on a Gram-negative strain of *Pseudomonas aeruginosa,* a synergy was observed. This property makes it possible, for example, to effectively treat patients with a reduced content of antibiotic, which may reduce the appearance of resistance to the antibiotics.

According to another aspect, the invention provides compounds of formula (I) for their use in the treatment of parasitic or viral infections of man or of animals, such as malaria, feline immunodeficiency virus (FIV), feline infectious peritonitis (FIP), toxoplasmosis, leishmaniasis, echinococcosis, ehrlichiosis, Rubarth's disease, leptospirosis, canine distemper, canine parvovirus infection, piroplasmosis, kennel cough or whooping cough, dirofilariasis, feline leucovirus (FeLV), coryza, typhus or feline panleucopenia. The compounds according to the invention can also be used as antiviral agent or as anticancer agent.

According to a specific aspect, the invention relates to the compound SA-10, SA-Y or SA-Z for its use in the treatment of parasitic or viral infections of man or of animals, such as malaria, feline immunodeficiency virus (FIV), feline infectious peritonitis (FIP), toxoplasmosis, leishmaniasis, echinococcosis, ehrlichiosis, Rubarth's disease, leptospirosis, canine distemper, canine parvovirus infection, piroplasmosis, kennel cough or whooping cough, dirofilariasis, feline leucovirus (FeLV), coryza, typhus or feline panleucopenia. The compound SA-10, SA-Y or SA-Z according to the invention can also be used as antiviral agent or as anticancer agent.

According to a specific aspect, the compounds of formula (I) are administered in combination with another antimalarial compound. Advantageously, the compounds of formula (I) make it possible to potentiate the activity of antiparasitic compounds, in particular antimalarial compounds.

Pharmaceutical Composition

According to a second subject matter, the invention relates to a pharmaceutical or veterinary composition comprising a compound of formula (I) and a pharmaceutically acceptable excipient:

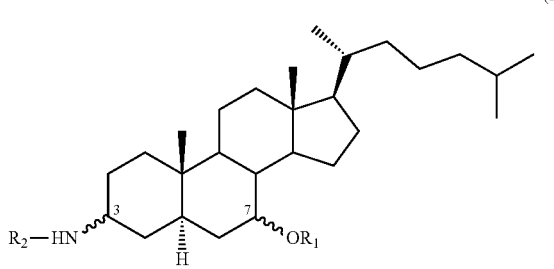

(I)

in which:

$R_1$ and $R_2$ are as defined above, and also the stereoisomers, mixtures of stereoisomers and/or the pharmaceutically acceptable salts of the compounds of formula (I).

According to a preferred aspect, the compound 3β-(norspermino)-7α-hydroxy-5α-cholestane and the compounds with the following formulae are excluded:

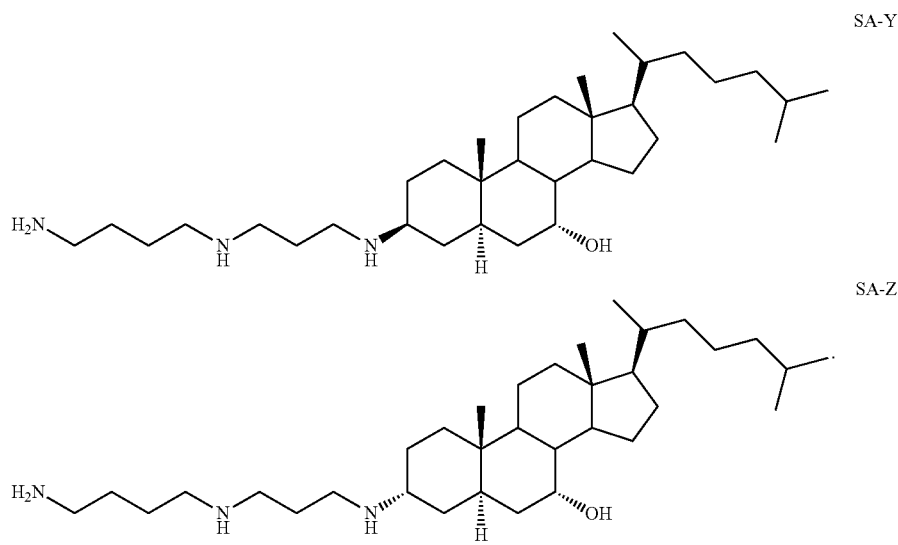

According to a preferred aspect, the compounds for which p=1, q=0, m=3, n=3 or 4, and X=NH are excluded.

According to a preferred aspect, it is understood that:
when p=1 and q=0, then m+n≠6 and 7,
when p=0 and q=1, then m+n+o≠6 and 7.

According to a specific embodiment, the invention relates to the compounds of formula (I) as described above with the exclusion of the compounds of formula (I) in which:

$R_1$ is H, $R_2$ is NHR and R is chosen from:

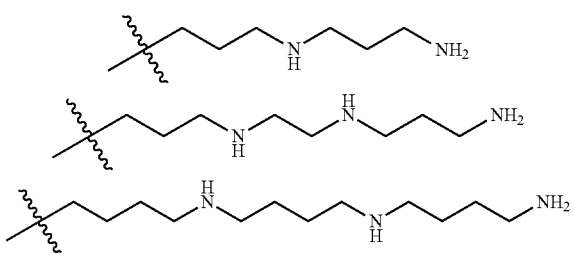

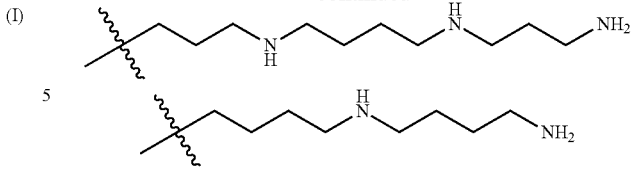

According to one aspect of the invention, pharmaceutical compositions are provided which additionally comprise a second antibiotic compound, in particular of the family of the beta-lactamines (penicillins/cephalosporins), aminosides, macrolides, polypeptides, sulfamides, quinolones, nitroimidazoles, nitrofuran derivatives, derivatives of the benzylpyrimidine nucleus, tetracyclines or phenicols, or a second antiparasitic compound, in particular antimalarial compound.

The pharmaceutical or veterinary compositions according to the invention can be presented in solid or liquid forms, for example intended for administration by the parenteral (intravenous, intramuscular, subcutaneous), oral or topical route.

They will thus be presented in the form of injectable solutions or suspensions or single-dose or multidose battles, in the form of bare or coated tablets, including sugar-coated tablets, of capsules, including hard gelatin capsules, of pills, of cachets, of powders, of granules, of suppositories or of rectal capsules.

Advantageously, the product according to the invention also comprises one or more additional ingredients well known to a person skilled in the art, such as, in particular, binding agents, granulating agents, lubricants, colorants, fillers, emulsifiers, minerals, film-forming agents, salts, stabilizers, buffers or vitamins. The stabilizers comprise the substances which have a tendency to increase the shelf life of the composition, such as preservatives, emulsifiers, thickeners, packaging gases, gelling agents, humectants, sequestering agents, synergistic agents or stabilizers.

For parental use, water, aqueous solutions, physiological saline solution or isotonic solutions are the most conveniently used vehicles.

For percutaneous use, in particular on the skin, human membranes or hair, in particular for solutions to be poured of "pour-on" or "spot-on" type in veterinary medicine, the normal excipients are polar or nonpolar aqueous or alcoholic solvents which promote transcutaneous passage, such as water, benzyl alcohol, vegetable and mineral oils, resuspending agents, antioxidants or surfactants; in particular, a mixture consisting of benzyl alcohol and/or of Labrasol and/or of propylene glycol laurate, as penetrating agent, can be used.

The doses can vary within wide limits (0.05 mg to 1000 mg) depending on the therapeutic indication and on the administration route, and also on the age and weight of the subject.

Compounds of Formula (I)

According to a third subject matter, the invention relates to compounds of formula (I):

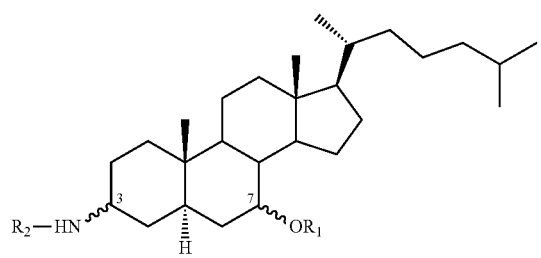
(I)

in which:
R$_1$ and R$_2$ are as defined above,
and also the stereoisomers, mixtures of stereoisomers and/or the pharmaceutically acceptable salts of the compounds of formula (I).

According to a preferred aspect, the compound 3β-(norspermino)-7α-hydroxy-5α-cholestane and the compounds having the following formulae are excluded:

According to a preferred aspect, the compounds for which p=1, q=0, m=3, n=3 or 4, and X=NH are excluded.

According to a preferred aspect, it is understood that:
when p=1 and q=0, then m+n≠6 and 7,
when p=0 and q=1, then m+n+o≠6 and 7.

Process for the Preparation of the Compounds of Formula (I)

The compounds of general formula (I) can be prepared by application or adaptation of any method known per se and/or within the scope of a person skilled in the art, in particular those described by Larock in Comprehensive Organic Transformations, VCH Pub., 1989, or application or adaptation of the processes described in the examples which follow.

According to another subject matter, the present invention thus also relates to the process for the preparation of the compounds of formula (I) which are described above, comprising a stage of reductive amination of the compound of formula (II) in the presence of an amine R$_2$NH$_2$, whereby the compound of formula (I) is obtained:

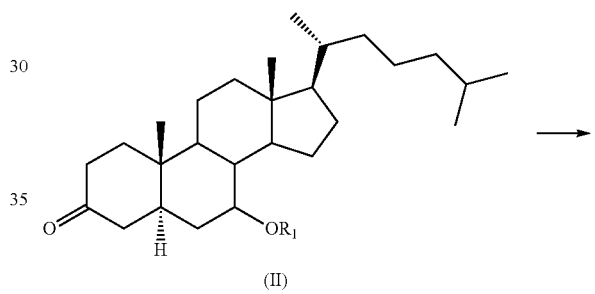
(II)

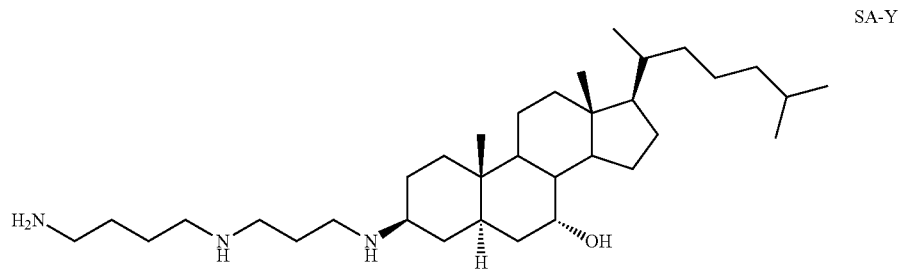
SA-Y

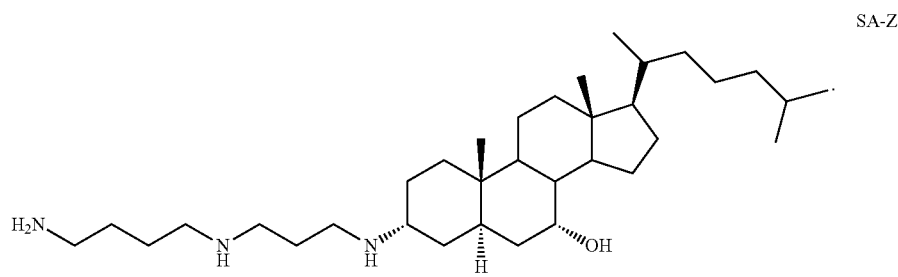
SA-Z

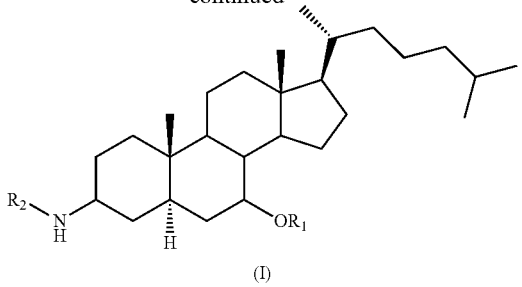

(I)

Optionally, said process can also comprise the stage consisting in isolating the product obtained.

The compound thus prepared can be recovered from the reaction mixture by conventional means. For example, the compounds can be recovered by distilling the solvent from the reaction mixture or, if necessary, after distillation of the solvent from the mixture of the solution, the remainder being poured into water, followed by an extraction with a water-immiscible organic solvent, and by distilling the solvent by the extract. In addition, the product can, if desired, be further purified by various techniques, such as recrystallization, reprecipitation or the various chromatography techniques, in particular column chromatography or preparative thin layer chromatography.

It will be appreciated that the compounds of use according to the present invention can contain several asymmetric centers. These asymmetric centers can be independently in the R or S configuration. It should be understood that the present invention comprises the stereoisomers, including enantiomers or diastereoisomers, and mixtures of these, including racemic mixtures, of compounds of formula (I) above. These stereoisomers can be separated from their mixtures by the application or the adaptation of known processes, for example chromatography techniques or recrystallization techniques, or they can be prepared separately from the appropriate stereoisomers of their intermediates.

The base products or the reactants used are commercially available and/or can be prepared by the application or the adaptation of known processes, for example of the processes as described in the Examples or their obvious chemical equivalents.

Definitions

According to the present invention, the "alkyl" radicals represent saturated, straight- or branched-chain, hydrocarbon radicals of 1 to 8 carbon atoms, in particular of 1 to 6 carbon atoms, preferably of 1 to 4 carbon atoms. Mention may in particular be made, when they are linear, of the methyl, ethyl, propyl, butyl, pentyl or hexyl radicals. Mention may in particular be made, when they are branched, of the isopropyl, tert-butyl, 2-methylbutyl, 2-methylpentyl and 1-methylpentyl radicals.

The term "aryl" group is understood to mean, within the meaning of the present patent application, a mono- or bicyclic aromatic hydrocarbon system of 6 to 10 carbon atoms. Mention may in particular be made, among aryl radicals, of the phenyl or naphthyl radical.

The term "heterocyclyl" group is understood to mean, within the meaning of the present patent application, a saturated, unsaturated or aromatic and mono- or bicyclic hydrocarbon system comprising one or more heteroatoms, such as O, N or S. The heterocyclyl groups include in particular heteroaryl or heterocycloalkyl groups.

The "heteroaryl" groups denote mono- or bicyclic aromatic systems having from 5 to 7 ring members (ring atoms), in particular from 5 to 6 ring numbers, and comprising one or more heteroatoms chosen from nitrogen, oxygen or sulfur. Mention may be made, among heteroaryl radicals, of imidazolyl, pyrazinyl, thienyl, oxazolyl, furazanyl or pyrrolyl.

The "heterocycloalkyl" radicals denote saturated mono- or bicyclic systems of 5 to 7 ring members (ring atoms), in particular of 5 to 6 ring members, and comprising one or more heteroatoms chosen from N, O or S. Mention may in particular be made, among heterocycloalkyls, of pyrazolidine, piperidine, morpholine or piperazine.

The expression "pharmaceutically acceptable salts" refers to the addition salts of inorganic and organic acids, which are pharmaceutically acceptable, and the addition salts of pharmaceutically acceptable bases, of the compounds of the present invention. These salts include acid addition salts, that is to say organic or inorganic acid salts of a compound comprising a basic functional group, such as an amine, or basic addition salts, that is to say alkali metal or organic salts of a compound comprising an acid functional group, such as a carboxylic acid. These salts can be prepared in situ during the final isolation and/or the purification of the compounds. In particular, the acid addition salts can be prepared by separately reacting the purified compound with an organic or inorganic acid and by isolating the salt thus formed. Examples of acid addition salts include hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthalate, mesylate, glucoheptonate, lactobionate, sulfamates, malonates, salicylates, propionates, methylenebis(β-hydroxynaphthoates), gentisic acid, isethionates, di(p-toluoyl)tartrates, methanesulfonates, ethanesulfonates, benzenesulfonates, p-toluenesulfonates, cyclohexyl sulfamates and quinate laurylsulfonate, and analogs (see, for example, S. M. Berge et al., "Pharmaceutical Salts", J. Pharm. Sci., 66, pp. 1-19 (1977)).

The basic addition salts can also be prepared by separately reacting the purified compound in its acid form with an organic or inorganic base and by isolating the salt thus formed. Examples of basic addition salts comprise sodium, potassium, calcium, barium, zinc, magnesium and aluminum salts. Sodium and potassium salts are preferred. The basic addition salts can in particular be prepared from alkali metal or alkaline earth metal hydrides or hydroxides which comprise sodium hydride, sodium hydroxide, potassium hydroxide, calcium hydroxide, aluminum hydroxide, lithium hydroxide, magnesium hydroxide or zinc hydroxide.

As used here, the term "pharmaceutically acceptable" refers to compounds, compositions and/or dosage forms which are, within the scope of a valid medical judgment, suitable for use in contact with the cells of human beings and lower animals without toxicity, irritation or induced allergic response and the like, and are proportional to a reasonable advantage/risk ratio.

As used here, the term "stereoisomer" refers to the optical isomers related to the two asymmetric carbon atoms located at the 3 position and at the 7 position in the formula (I) and includes the enantiomers and diastereoisomers of these compounds.

Other characteristics of the invention will become apparent in the examples which follow. These examples are given in order to illustrate the invention and are not intended to be limiting of the latter.

EXAMPLES

I. Synthesis of the Compounds of Formula (I)

All the syntheses were carried out with solvents purified according to the usual methods. The commercial reactants are used directly without prior purification.

The chemical structures synthesized were all confirmed by a proton ($^1$H) and/or carbon ($^{13}$C) NMR analysis in deuterated chloroform CDCl$_3$ or deuterated methanol CD$_3$OD on a device of Bruker AC 300 type. The chemical shifts δ are expressed in ppm. The recording frequencies of the nuclei and also the references used are as follows:

$^1$H NMR: 300 MHz, Si(CH$_3$)$_4$
$^{13}$C NMR: 75 MHz, Si(CH$_3$)$_4$

The abbreviations used for writing the $^1$H NMR spectrum are as follows:
s=singlet
d=doublet
t=triplet
q=quartet
m=broad unresolved peak The mass spectra were produced at the Spectropole of Aix-Marseille III. They are produced on the dry product using a Triple Quadrupole API III Plus spectrometer from Sciex. The sample is dissolved in 500 μl of CH$_2$Cl$_2$ and then diluted to 1/10$^4$ in a 3 mM solution of ammonium acetate in MeOH. The solution of the extract is introduced into the ionization source by infusion (syringe driver pump, Harvard Apparatus) at a flow rate of 5 μl/min.

The compounds of formula (I) were prepared according to the reaction scheme below:

Synthesis of 7-ketocholest-5-en-3β-ol 1

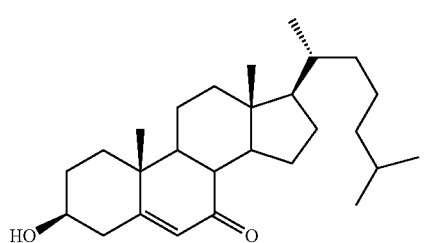

1

50 g of cholesterol (0.129 mol), 22 g of hydroxyphthalamide (0.135 mol) and 1.5 l of an ethyl acetate/acetone (1/1) mixture are placed in a reactor provided with a mechanical stirrer. The mixture is brought to 50° C. 200 mg of benzoyl peroxide are added and air is bubbled through for 72 h while adjusting the level of the solvent and while monitoring the handling by thin-layer chromatography. After 72 h, the solvent is evaporated under vacuum. The residue is dissolved in petroleum ether and washed with sodium carbonate until the orange coloration disappears. The organic phases are washed with a saturated NaCl solution and dried over MgSO$_4$. The solvent is driven off under vacuum and the sterol is dissolved in pyridine (200 ml). Cooling is carried out at 0° C. and 1 g of CuCl$_2$ is added. The solution is stirred for 24 h (return from 0° C. to ambient temperature). The solution obtained is poured onto a water/ice mixture. Extraction is carried out with ethyl acetate and washing is carried out with a saturated CuSO$_4$ solution. After separation of the phases, the organic phase is washed with a 0.1N HCl solution and dried over MgSO$_4$. After evaporation of the solvent, the residue is chromatographed on silica gel (petroleum ether/ethyl acetate 1/1). The expected ketone is obtained in the form of an off white solid with a yield of 70%.

$^1$H NMR: δ=5.45-5.75 (m, 1H), 3.475-3.75 (m, 1H), 2.125-2.75 (m, 4H), 1.75-2.075 (m, 6H), 0.8-1.7 (m, 37H), 0.45-0.75 (m, 4H); $^{13}$C NMR: δ=202.81, 165.59, 126.49, 70.89, 55.17, 50.34, 45.80, 43.49, 39.87, 38.67, 36.57, 36.11, 28.40, 26.72, 24.22, 23.22, 22.96, 21.61, 19.26, 17.71, 12.37.

Synthesis of 7-ketocholest-5-en-3β-yl acetate 2

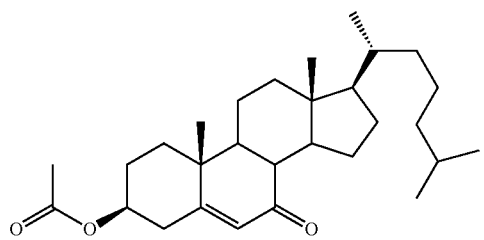

2

3 mmol of 7-ketocholest-5-en-3β-ol 1 are dissolved in pyridine (25 ml) in a two-necked round-bottomed flask equipped with a reflux condenser, and 9 mmol of acetic anhydride are added. The mixture is left under magnetic stirring in an ice bath for 24 h. The pyridine is evaporated under high vacuum and then the solid obtained is resuspended in CH$_2$Cl$_2$ (15 ml). An extraction with copper sulfate is then carried out and the organic phase is dried over MgSO$_4$, filtered and then dried under high vacuum. The product is purified by chromatography on silica gel (eluent: petroleum ether/ethyl acetate 9/1) (Yd 94%).

$^1$H NMR: δ=5.65-5.7 (d, 1H), 4.6-4.75 (m, 1H), 0.6-2.6 (m, 44H); $^{13}$C NMR: δ=201.90, 170.24, 163.81, 126.68, 72.19, 54.75, 49.93, 49.78, 45.38, 43.08, 39.44, 38.64, 38.28, 37.72, 36.15, 35.98, 35.69, 31.90, 28.50, 27.96, 27.32, 26.28, 23.80, 22.77, 22.52, 21.24, 21.14, 18.84, 17.22, 11.93.

Synthesis of 7-ketocholestan-3β-yl acetate 3

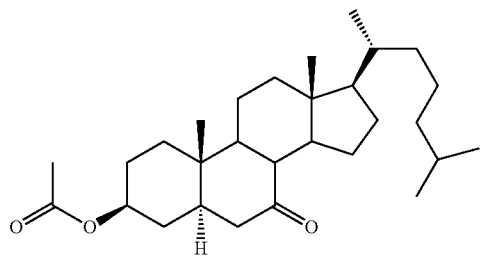

3

3.04 g (6.87 mmol) of 7-ketocholest-5-en-3β-yl acetate 2 and 1.1 g (approximately 15 mol %) of Pd/C (10%) are introduced into 50 ml of $CH_2Cl_2$ in a stainless steel reactor. The reactor is placed under 50 bar of hydrogen and under vigorous stirring for 12 h. After filtration through celite and evaporation of the solvent under vacuum, the product is obtained virtually pure and with a quantitative yield. It will be used as is in the following stage.

$^1$H NMR: δ=4.62-4.70 (m, 1H), 0.64-2.39 (m, 47H); $^{13}$C NMR: δ=211.44, 170.38, 72.71, 54.95, 49.90, 48.82, 46.43, 45.34, 42.45, 39.42, 38.65, 36.09, 35.89, 35.60, 33.79, 28.35, 27.93, 26.34, 24.93, 23.72, 22.74, 22.51, 22.15, 21.27, 18.73, 12.01, 11.65.

Synthesis of the mixture of
7β-hydroxycholestan-3β-ol 4a and
7α-hydroxycholestan-3β-ol 4b

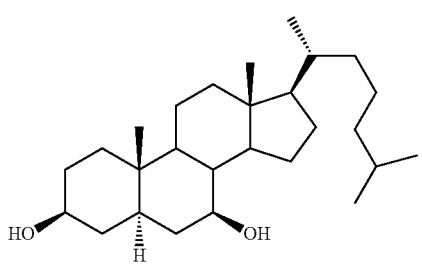

4a

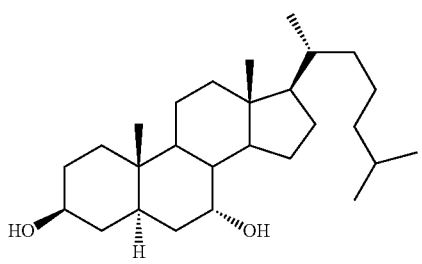

4b 530 mg of lithium aluminum hydride (13.8 mmol) are placed in 100 ml of anhydrous THF in a two-necked round-bottomed flask. A solution of 7-ketocholestan-3β-yl acetate 3 (1.5 g, 3.3 mmol) dissolved in 15 ml of THF is slowly added at 0° C. After stirring at ambient temperature for 12 h, hydrolysis is carried out with KOH (30%) solution (1.2 ml). Stirring is continued for 1 h, then filtration is carried out through celite and rinsing is carried out with MeOH, and then the solvents are evaporated under vacuum. The product in the form of a mixture of isomers (α/β 50/50) is purified by chromatography on silica gel (eluent: petroleum ether/ethyl acetate 8/2) (Yd 95%).

$^1$H NMR: δ=0.6-3.82 (m, 48H); $^{13}$C NMR: δ=75.11, 71.08, 70.99, 67.96, 62.57, 56.45, 56.08, 55.68, 55.19, 51.85, 50.51, 45.83, 43.95, 43.35, 42.60, 42.00, 39.46, 37.62, 37.11, 36.54, 36.24, 35.73, 35.51, 34.88, 31.30, 29.82, 28.05, 27.95, 26.86, 23.79, 23.71, 22.76, 22.51, 21.56, 20.96, 18.60, 12.40, 12.11, 11.79, 11.20.

Synthesis of 3-keto-7β-hydroxycholestane 5a and
3-keto-7α-hydroxycholestane 5b

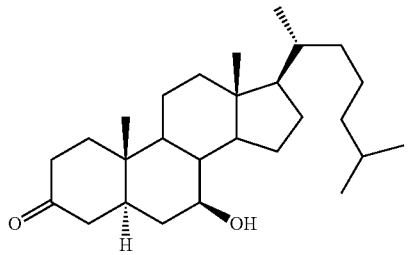

5a

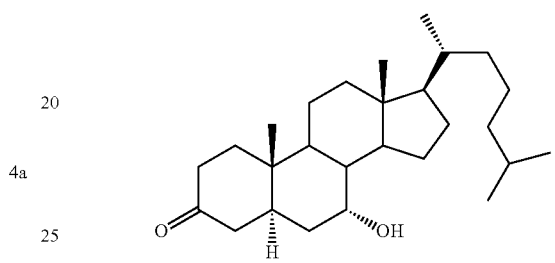

5b 1.28 g of mixture of 7β-hydroxycholestan-3β-ol 4a and 7α-hydroxycholestan-3β-ol 4b are placed in 150 ml of toluene and 3.6 g of silver carbonate on celite in a single-necked round-bottomed flask surmounted by a Dean & Stark apparatus. The system is brought to reflux of the toluene for 24 h. After cooling the mixture is filtered through celite. Purification is carried out by chromatography on silica gel (eluent: petroleum ether/ethyl acetate 7/3) and the two pure isomers 5b (fraction 1) and 5a (fraction 2) are thus obtained with nonoptimized yields of 31% and 25% respectively.

5a $^1$H NMR: δ=3.05-3.55 (m, 1H), 2.2-2.6 (m, 3H), 0.4-1.92 (m, 42H); $^{13}$C NMR: δ=211.55, 74.66, 55.61, 55.24, 51.83, 44.18, 43.94, 43.66, 39.90, 39.54, 38.12, 35.72, 35.16, 28.75, 28.06, 23.89, 22.87, 22.62, 21.80, 18.84, 12.22, 11.63.

5b $^1$H NMR: δ=3.3-3.85 (m, 1H), 0.60-2.65 (m, 45H); $^{13}$C NMR: δ=211.36, 71.08, 57.18, 56.53, 54.33, 47.13, 39.86, 38.32, 37.07, 36.49, 36.08, 31.10, 30.44, 28.43, 28.39, 24.38, 24.20, 23.20, 22.93, 21.92, 19.03, 13.53, 12.40.

Synthesis of the Aminosteroidal Derivatives SA-1
to SA-12

The aminosteroidal derivatives were all produced according to the same procedure. Let us consider the example of the molecule SA-1.

3.3 equivalents of spermine (171 mg, 0.82 mmol) are dissolved in 5 ml of MeOH in a two-necked round-bottomed flask placed under argon and then 300 μl of Ti(O(i-Pr))$_4$ (1 mmol) are added. After stirring for 5 minutes, 102 mg of 3-keto-7α-hydroxycholestane 5b (0.25 mmol) are added to the mixture. After stirring for 24 hours, the round-bottomed flask is placed at −78° C. and then 40 mg of NaBH$_4$ (1 mmol) are added with stirring. After 2 hours and returning to ambient temperature, 1 ml of water is added in order to terminate the reaction. After stirring for an additional 1 h, the mixture is filtered through celite. The filtrate is evaporated under vacuum and the product is purified by chromatography on silica gel (eluent: $CH_2Cl_2$/MeOH/NH$_4$OH (7/3/1)).

3β-Spermino-7α-hydroxy-5α-cholestane SA-1

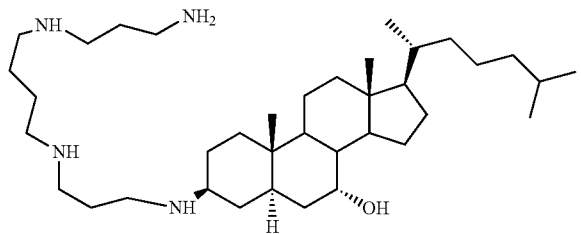

Yd: 54%. $^1$H NMR: δ=3.16 (m, 1H), 2.44-2.65 (m, 13H), 1.96 (m, 5H), 0.89-1.64 (m, 57H); $^{13}$C NMR: δ=71.65, 57.46, 56.03, 51.04, 47.98, 47.64, 46.61, 45.34, 42.76, 40.80, 40.60, 40.02, 39.82, 39.74, 38.62, 37.16, 34.58, 33.12, 29.45, 28.30, 28.12, 25.11, 24.30, 24.28, 22.68, 20.91, 18.73, 13.56, 11.92.

3β-Spermino-7β-hydroxy-5α-cholestane SA-2

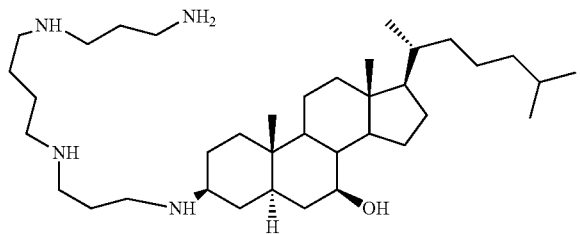

Yd: 49%. $^1$H NMR: δ=3.05 (m, 1H), 2.44-2.65 (m, 13H), 1.95 (m, 5H), 0.89-1.63 (m, 57H); $^{13}$C NMR: δ=73.95, 57.46, 56.03, 51.04, 47.98, 47.64, 46.84, 45.84, 42.66, 41.80, 40.75, 40.39, 39.82, 39.65, 37.45, 37.26, 36.28, 26.26, 34.58, 33.97, 29.45, 28.30, 28.08, 25.35, 25.12, 24.30, 24.28, 21.98, 20.90, 18.73, 13.54, 11.89.

3β-Norspermidino-7β-hydroxy-5α-cholestane SA-3

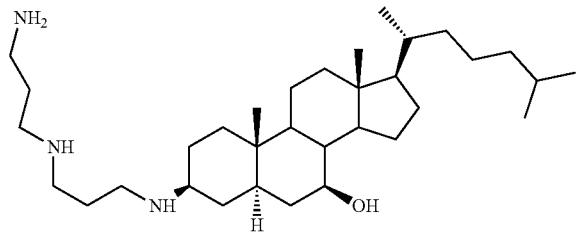

Yd: 46%. $^1$H NMR: δ=3.14 (m, 1H), 2.55-2.65 (m, 8H), 2.01 (m, 4H), 1.01-1.83 (m, 50H); $^{13}$C NMR: δ=73.46, 57.64, 56.03, 52.39, 47.47, 46.54, 45.98, 42.79, 41.20, 40.78, 40.54, 40.22, 40.10, 37.12, 37.02, 36.28, 36.26, 34.58, 33.91, 29.41, 29.12, 28.23, 25.62, 23.41, 23.12, 22.68, 20.84, 18.74, 13.68, 11.97.

3β-(1,3-Diaminopropane)-7β-hydroxy-5α-cholestane SA-4

Yd: 54%. $^1$H NMR: δ=3.21 (m, 1H), 2.53-2.60 (m, 4H), 0.89-1.81 (m, 51H); $^{13}$C NMR: δ=71.22, 57.33, 55.89, 52.02, 46.01, 41.78, 40.96, 40.35, 39.92, 39.25, 39.02, 37.98, 37.11, 36.58, 36.45, 34.75, 34.25, 29.68, 28.64, 28.02, 23.56, 23.12, 22.68, 20.87, 18.98, 14.02, 11.92.

3β-(1,4-Diaminobutane)-7β-hydroxy-5α-cholestane SA-5

Yd: 48%. $^1$H NMR: δ=3.17 (m, 1H), 2.55-2.63 (m, 4H), 0.99-1.83 (m, 53H); $^{13}$C NMR: δ=71.23, 56.03, 55.66, 51.02, 48.29, 42.78, 41.19, 40.98, 40.02, 39.74, 39.65, 38.54, 37.14, 36.54, 36.45, 35.02, 34.89, 29.54, 29.45, 28.30, 28.08, 25.33, 24.85, 24.12, 22.67, 20.91, 18.76, 13.56, 11.90.

3β-(Tris(2-aminoethyl)amine)-7β-hydroxy-5α-cholestane SA-6

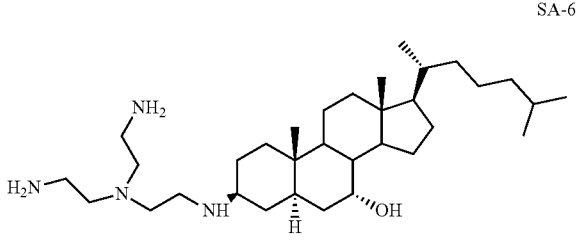 [SMILES: CC(C)CCC[C@@H](C)[C@H]1CCC2C3C(CC[C@@]21C)[C@@]1(C)CC[C@H](NCCN(CCN)CCN)C[C@@H]1C[C@H]3O]

Yd: 29%. ¹H NMR: δ=3.12 (m, 1H), 2.42-2.75 (m, 10H), 1.89 (m, 6H), 1.01-1.87 (m, 47H); ¹³C NMR: δ=71.35, 57.70, 56.32, 55.24, 54.44, 51.04, 43.59, 42.98, 40.80, 40.12, 40.02, 40.00, 38.88, 38.32, 36.27, 35.97, 35.85, 35.02, 34.87, 29.18, 28.30, 28.08, 24.22, 23.85, 22.67, 20.89, 18.79, 13.54, 11.94.

3β-(1,5-Diaminopentane)-7α-hydroxy-5α-cholestane SA-7

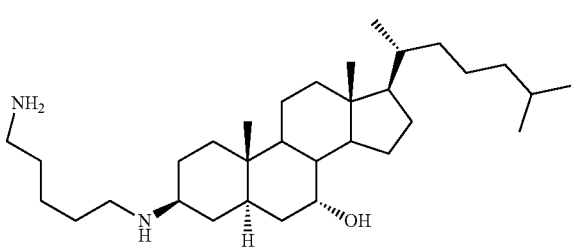

Yd: 32%. ¹H NMR: δ=3.14 (m, 1H), 2.54-2.60 (m, 5H), 0.95-1.89 (m, 54H); ¹³C NMR: δ=71.90, 56.87, 52.43, 51.92, 48.71, 47.38, 43.37, 42.57, 41.02, 40.51, 39.71, 36.81, 36.51, 36.46, 36.38, 34.38, 34.12, 32.10, 29.84, 29.34, 28.68, 24.89, 22.44, 18.56, 12.34.

3β-(1,4-Bis(3-aminopropyl)piperazine)-7β-hydroxy-5α-cholestane SA-8

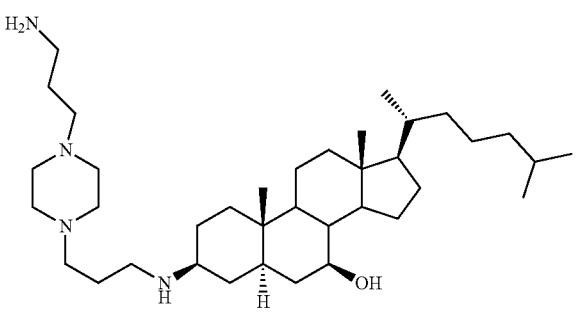

Yd: 48%. ¹H NMR: δ=3.21 (m, 1H), 2.52-2.66 (m, 6H), 0.97-1.95 (m, 63H); ¹³C NMR: δ=73.12, 56.42, 52.4, 51.91, 48.70, 47.32, 43.35, 42.55, 41.0, 40.57, 39.77, 36.89, 36.59, 36.40, 36.34, 34.38, 34.14, 32.12, 29.85, 29.37, 28.62, 24.88, 22.41, 22.41, 18.13, 12.33.

3β-(1,4-Bis(3-aminopropoxy)butane)-7β-hydroxy-5α-cholestane SA-9

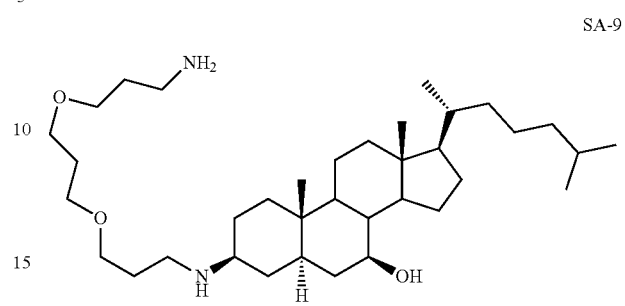

Yd: 42%. ¹H NMR: δ=3.13 (m, 1H), 2.51-2.60 (m, 4H), 0.97-1.98 (m, 63H); ¹³C NMR: δ=73.80, 68.33, 68.12, 66.44, 66.06, 57.23, 51.95, 51.72, 48.84, 43.35, 43.02, 41.92, 41.63, 39.32, 38.25, 36.45, 35.77, 35.62, 35.12, 34.80, 33.42, 33.12, 29.87, 28.75, 26.33, 26.01, 22.12, 21.84, 18.63, 11.92.

3β-(Norspermino)-7α-hydroxy-5α-cholestane SA-10

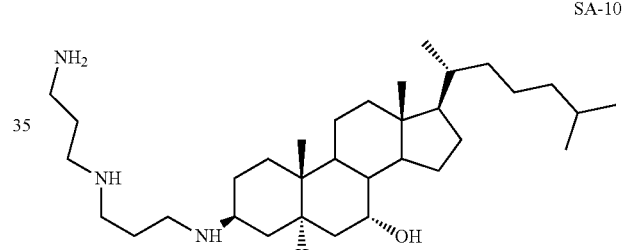

Yd: 48%. ¹H NMR: δ=3.13 (m, 1H), 2.55-2.66 (m, 8H), 1.01-2.02 (m, 54H); ¹³C NMR: δ=71.9, 57.64, 56.03, 52.39, 47.50, 46.54, 45.98, 42.79, 41.20, 40.78, 40.54, 40.22, 40.10, 37.12, 37.02, 36.27, 36.26, 34.58, 33.81, 29.41, 29.12, 28.23, 25.62, 23.41, 23.12, 22.67, 20.84, 18.04, 13.50, 11.87.

3β-(1-(3-Aminopropyl)imidazole)-7α-hydroxy-5α-cholestane SA-11

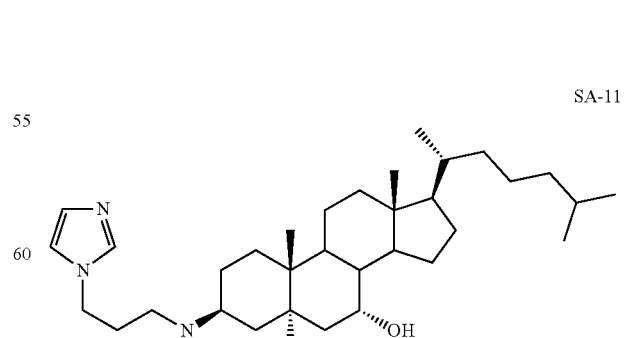

Yd: 22%. ¹H NMR: δ=3.18 (m, 1H), 2.56-2.66 (m, 4H), 1.09-2.01 (m, 42H); ¹³C NMR: δ=139.81, 126.32, 123.27, 71.68, 57.28, 52.39, 47.57, 46.78, 45.98, 42.79, 41.14, 40.88, 40.14, 40.02, 40.00, 37.12, 37.02, 36.26, 36.26, 34.53, 33.82, 29.41, 29.12, 28.23, 25.62, 23.41, 23.12, 22.66, 20.84, 18.14, 13.50, 11.87.

3β-(1-(3-Aminopropyl)morpholine)-7α-hydroxy-5α-cholestane SA-12

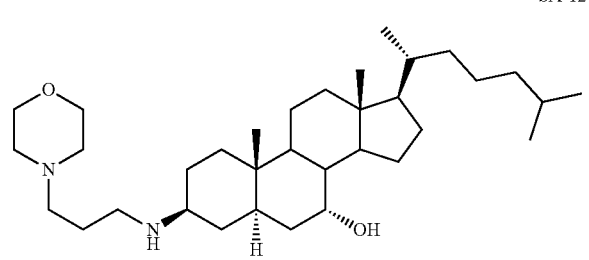

SA-12

Yd: 34%. $^1$H NMR: δ=3.14 (m, 1H), 2.56-2.66 (m, 6H), 0.94-2.02 (m, 55H); $^{13}$C NMR: δ=72.01, 71.09, 70.95, 55.44, 55.12, 55.03, 52.39, 47.42, 47.24, 45.88, 42.19, 41.00, 40.87, 40.54, 40.22, 40.11, 37.12, 37.02, 36.27, 36.26, 35.58, 34.81, 29.41, 29.72, 28.21, 25.62, 23.41, 23.03, 22.87, 21.82, 19.04, 13.26, 11.19.

II. Evaluation of the Biological Activities

A. Intrinsic Antibacterial Activities of the Compounds of Formula (I)

1) Preparation of the Preculture

Two tubes were prepared:
A negative control (2 ml of sterile culture medium)
A positive control (1940 μl of culture medium+40 μl of DMSO+20 μl of the bacterial suspension) from a defrosted biological strain (the preservation of the biological strains is carried out at −80° C. in glycerol). The strains used are *S. aureus* ATCC 25923, *E. coli* ATCC 25922, *P. aeruginosa* ATCC 27853, *C. albicans* CIP 1180-79 and *E. faecalis* CIP 103015.

The tubes were incubated in an Infors at 37° C. for 24 hours at 100 revolutions per minute.

The microorganisms were handled under a hood in the laboratory of L2 type and, before any handling operation, a UV cycle was programmed and only sterile material was used. A test of toxicity of the solvents (methanol, ethanol, DMSO) was carried out and the latter proved to be nontoxic at concentrations of less than or equal to 2%. The chemical molecules to be tested were prepared in a DMSO/methanol (50/50) mixture at a concentration of 5 mg/ml.

2) Preparation of the Microplate for the Determination of the Minimum Inhibitory Concentration (MIC)

After incubating for 24 h, the optical density was measured using a spectrophotometer at 600 nm by withdrawing 100 μl of the bacterial suspension diluted in 900 μl of the sterile culture medium. This test required the use of a 96-well plate and the necessary volume of the microbial suspension to be inoculated was calculated for an OD corresponding to a value equal to 0.01 in each well. In this plate, the first line corresponded to the negative control (195 μl of sterile culture medium in each well), the second line to the positive control (inoculated culture medium with the addition of 2% of DMSO), the third line was charged twice with bacterial suspension, 8 μl of product to be tested was placed in each well. Subsequently, cascade half dilution was carried out starting from this line.

The first column was used as inhibition control. A sterile filter was subsequently placed on the microplate, allowing the passage of gases but not of contaminants. The microplate was incubated at 37° C. in a humid atmosphere for 24 h.

NB: The medium used is the Mueller-Hinton (MH) medium for the bacteria. All the tests were carried out in duplicate.

3) Reading of the Results

After incubation, the filter was replaced with a transparent film and subsequently reading of OD was carried out in an IEMS plate spectrophotometer at 620 nm. A calculation of the minimum inhibitory concentration (MIC) was carried out.

TABLE I

Intrinsic antibacterial activities of the compounds of formula (I)

| | MIC (μg/ml) | | | | | |
|---|---|---|---|---|---|---|
| Compounds | *S. aureus* ATCC 25923 | *S. aureus* Methicillin-resistant | *S. faecalis* | *C. albicans* | *E. coli* ATCC 25922 | *P. aeruginosa* ATCC 27853 |
| Squalamine | 4 | 4 | 4 | 2 | 12 | 20 |
| SA-1 | 4 | 2 | 2 | 2 | 16 | 32 |
| SA-2 | 4 | 2 | 2 | 2 | 32 | 32 |
| SA-3 | 5 | 2.5 | 2.5 | 2.5 | 20 | 40 |
| SA-4 | 4 | 2 | 2 | 2 | 32 | 32 |
| SA-5 | 4 | 4 | 4 | 4 | 32 | 32 |
| SA-6 | 5 | 5 | 2.5 | 2.5 | 20 | 40 |

B. Comparison of the Cytotoxicity and of the Antibacterial Activities of the Compounds of Formula (I) with Those of the Compounds (IIa), (IIb), (IIc) and (IId) Disclosed in the Application WO 2011/067501

The WST-1 test was used to measure the cytotoxic activity of the products. This is a colorimetric test which makes it possible to measure the viability and the degree of cell proliferation. It is based on the cleaving of colorless tetrazolium salts WST-1 (4-[3-(4-iodophenyl)-2-(4-nitrophenyl)-2H-5-tetrazolio]-1,3-benzenedisulfonate) by mitochondrial dehydrogenases to give a yellow-colored formazan derivative, which are quantifiable by spectrophotometry at 420-480 nm.

The WST-1 test was carried out on Chinese hamster ovary cells. The CHO-K1 cells (ATCC, USA) are kept cultured in McCoy's 5 A medium additivated with 10% of fetal calf serum, with 2 mM of L-glutamine and with a penicillin/streptomycin mixture (100 U/ml: 10 μg/ml). Incubating is carried out at 37° C. under an atmosphere enriched in $CO_2$ (5%) and subculturing is carried out every two days.

The cells are transferred into 96-well plates (25 000 cells/ml) in complete McCoy's 5 A medium and are maintained at 37° C. for 24 h under a humid atmosphere enriched in $CO_2$ (5%). Increasing concentrations of test products are added to the wells in duplicate tests and 8 growth controls containing the cells in the medium alone are included in each series of tests. After 24 hours at 37° C. (5% of $CO_2$), the culture medium is removed, the cells are rinsed in phosphate buffer (PBS) and 50 µl of PBS containing 10% of WST-1 reactant are added to each well. After incubating at 37° C. for 20 minutes, the results are read by spectrophotometry at 450 nm.

The results are expressed in the form of dose-response relationships, modeled by a nonlinear regression analysis using the TableCurve software. The 50% Inhibitory Concentration ($IC_{50}$) represents the concentration of product capable of reducing cell viability by 50%.

The following compounds (IIa), (IIb), (IIc) and (IId) were prepared by following the synthesis protocol disclosed in the application WO 2011/067501:

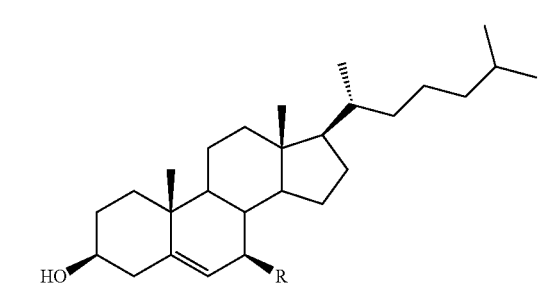

IIa

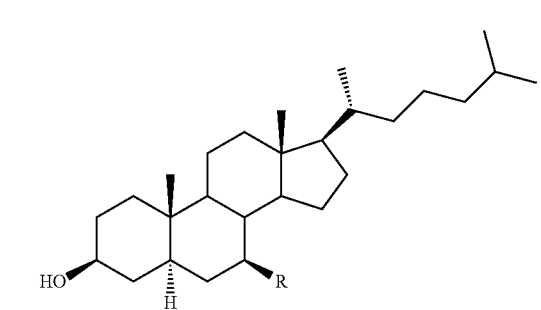

IIb

Examples
R =

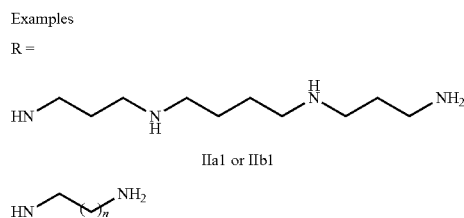

IIa1 or IIb1

IIa2 or Ib2 n = 2
IIa3 or IIb3 n = 3

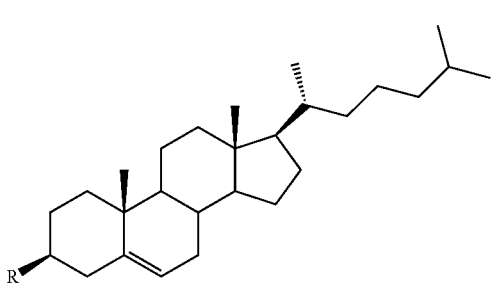

IIc

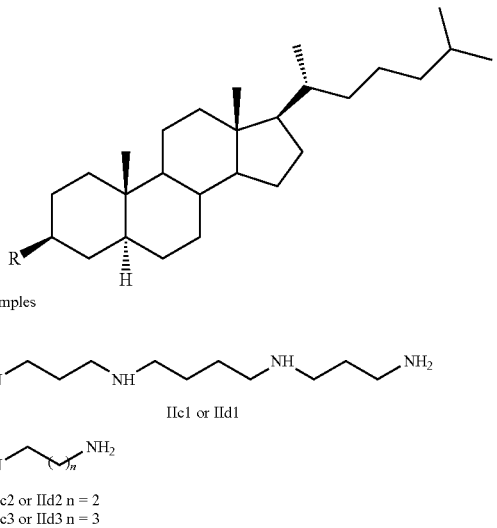

IId

Examples
R =

H₂N⌒⌒NH⌒⌒⌒NH⌒⌒⌒NH₂

IIc1 or IId1

H₂N⌒⌒ₙNH₂

IIc2 or IId2 n = 2
IIc3 or IId3 n = 3

The minimum inhibitory concentrations (MICs) and the cytotoxicity ($IC_{50}$) were evaluated according to the experimental protocols above.

TABLE II

Comparison of the intrinsic antibacterial activities of the compounds of formula (I) according to the invention with those of the compounds of the state of the art

| | MIC (µg/ml) | | |
|---|---|---|---|
| Compound | S. aureus (Methicillin-resistant) | E. coli | $IC_{50}$ CHO (µM) |
| IIa1 or IIb1 | 5 | 10 | <5 |
| IIa2 or IIb2 | 3.125 | 3.125 | <5 |
| IIa3 or IIb3 | 3.125 | 3.125 | <5 |
| IIc1 or IId1 | 3.125 | >50 | <5 |
| IIc2 or IId2 | 12.5 | >50 | <5 |
| IIc3 or IId3 | 12.5 | >50 | <5 |
| SA1 | 2 | 16 | 15 |
| SA2 | 2 | 32 | 50 |
| SA3 | 2.5 | 20 | 32 |
| SA4 | 2 | 32 | 9 |
| SA5 | 4 | 32 | 15 |
| SA6 | 5 | 20 | 46 |

It is found that the compounds of formula (I) are less cytotoxic than the compounds IIa, IIb, IIc and IId tested and exhibits a greater antibacterial activity than that of the compounds IIc and IId with regard to the *E. coli* Gram-negative bacteria.

C. Potentiating of the Activity of Conventional Antibiotics in the Presence of the Aminosteroidal Derivatives of Formula (I)

Example of Preparation of the Microplate for the Determination of the Minimum Inhibitory Concentration (MIC) of Doxycycline in the Presence of an Aminosteroidal Derivative This method requires the use of a 96-well plate; 100 µl of a liquid culture medium are deposited in each well and then inoculated with the microbial suspension prepared above. The necessary volume to be inoculated is calculated for an OD of 0.01, which corresponds to approximately 5×10⁶ bacteria in each well. In this plate, the first line corresponds to a negative control (200 μl of sterile culture medium in each well), the second line to a positive control (100 μl of sterile culture medium+100 μl of a bacterial suspension), the third line contains 192 μl of culture medium; 8 μl of aminosteroidal product to be tested are placed in each well. Subsequently, cascade dilution is carried out starting from this line. 8 μl of a doxycycline solution (1 mg dissolved in 20 ml) are subsequently added to each well of lines 3 to 8, in order to obtain a final concentration of antibiotic of 2 μg/ml. 92 μl of bacterial suspension are subsequently added to lines 3 to 8. The results (the determination of the MIC (2 μg/ml of doxycycline) in the presence of X μg/ml of aminosteroidal derivative) are read after incubating at 37° C. for 24 h in a humid atmosphere. After incubating at 37° C. for 24 h, 40 μl of nitrotetrazolium iodide are added to each well, making it possible to reveal the presence of living bacteria by coloring the medium pink.

In these first tests, the aim was to demonstrate or not a synergy of the aminosteroidal derivatives in the presence of a low concentration of two conventional antibiotics: doxycycline and chloramphenicol.

It should first of all be mentioned that, with regard to the Gram-negative strain of *P. aeruginosa* (PAO1), doxycycline has an MIC of 40 μg/ml and chloramphenicol an MIC of 1024 μg/ml.

The use of low amounts of aminosteroidal derivatives makes it possible to restore (to reduce) the necessary concentration of antibiotic to kill the strain under consideration. The results are recorded in the table below:

TABLE III

Potentiating of the activity of the conventional antibiotics in the presence of the aminosteroidal derivatives of formula (I)

| Compounds | Doxycycline concentration used (2 μg/ml) | Chloramphenicol concentration used (4 μg/ml) |
|---|---|---|
| Squalamine | 1.75 | 1.75 |
| SA-1 | 4 | 16 |
| SA-2 | 4 | 16 |
| SA-3 | 5 | 10 |
| SA-6 | 2.5 | 20 |

Concentration of compound necessary in order to restore the activity of the antibiotic under consideration (μg/ml)

A very good synergy of certain compounds with doxycycline is observed, thus restoring the activity of this antibiotic at low concentrations of use (2 μg/ml). In the case of chloramphenicol, the results are also encouraging since the MIC changes from 1024 to 4 μg/ml for fairly low doses of compounds to be added.

REFERENCES (1) Alhanout K, Brunel J M, Raoult D and Rolain J M, In vitro antibacterial activity of aminosterols against multidrug-resistant bacteria from patients with cystic fibrosis, J. Antimicrob. Chemother., 2009, October, 64(4), 810-4.
(2) Loncle et al., Tetrahedron, 2007, 63, 12968-12974.
(3) Salmi et al., European Journal of Medicinal Chemistry, 2008, 43, 540-547.
(4) Salmi et al., Letters in Drug Design & Discovery, 2008, 5, 169-172.
(5) Salmi et al., Journal of Enzyme Inhibition and Medicinal Chemistry, 2008, 23, 860-865.
(6) Loncle et al., Letters in Drug Design & Discovery, 2008, 5, 388-393.
(7) Salmi et al., Tetrahedron, 2008, 64, 4453-4459.
(8) Williams J I et al., Squalamine treatment of human tumors in nu/nu mice enhances platinum-based chemotherapies, Clin. Cancer Res., 2001 March, 7(3), 724-733.
(9) Daniel Amsterdam, "Susceptibility testing of antimicrobials in liquid media" in Antibiotics in Laboratory Medicine. 5th Edition. Editor Victor Lorian. Lippincott Williams and Wilkins, 2005, Philadelphia, USA.

The invention claimed is:

1. A method of treating a disease in a human or animal comprising administering to the human or animal a compound of formula (I):

(I)

[Chemical structure showing steroid backbone with $R_2$—HN on position 3 and $OR_1$ on position 7]

in which:
$R_1$ is chosen from H, $SO_3H$, a $C_1$-$C_8$ alkyl group, a $C_6$-$C_{10}$ aryl group or a C(=O)$R_{13}$ group,
$R_2$ is —(CR$_3$R$_4$)$_m$—(X)$_p$—(CR$_5$R$_6$)$_n$—[(Y)—CR$_7$R$_8$)$_o$]$_q$—NR$_9$R$_{10}$,
$R_3$, $R_4$, $R_5$, $R_6$, $R_7$ and $R_8$ are, in each case, identical or different, each independently chosen from H, $C_1$-$C_8$ alkyl, $C_6$-$C_{10}$ aryl and C(=O)O$R_{14}$;
$R_9$ and $R_{10}$, which are identical or different, are each independently chosen from H, $C_1$-$C_8$ alkyl or a —(CH$_2$)$_r$—NH$_2$ group or together form a 5- to 7-membered heterocyclyl group optionally substituted by one to three $R_{14}$ groups;
X and Y, which are identical or different, are in each case each independently chosen from NR$_{13}$, O or a 5- to 6-membered nitrogenous heterocyclyl group,
$R_{11}$ and $R_{12}$ are each independently chosen from a $C_1$-$C_8$ alkyl group or a $C_6$-$C_{10}$ aryl group,
$R_{13}$ is H, a $C_1$-$C_6$ alkyl group or a —(CH$_2$)$_s$—NH$_2$ group;
$R_{14}$ is a =O or =S group;
m is an integer between 1 and 5;
n is an integer between 1 and 5,
o is an integer between 1 and 5,
p is 0 or 1,
q is 0, 1, 2 or 3,
r is an integer between 1 and 4,
s is an integer between 1 and 5,
or a stereoisomer, mixture of stereoisomers or pharmaceutically acceptable salt thereof, the compound of formula I excludes 3β-(norspermino)-7α-hydroxy-5α-cholestane and compounds having the formula:

SA-Y

[Chemical structure: $H_2N$—(chain)—NH—(chain)—NH—(chain)]

-continued

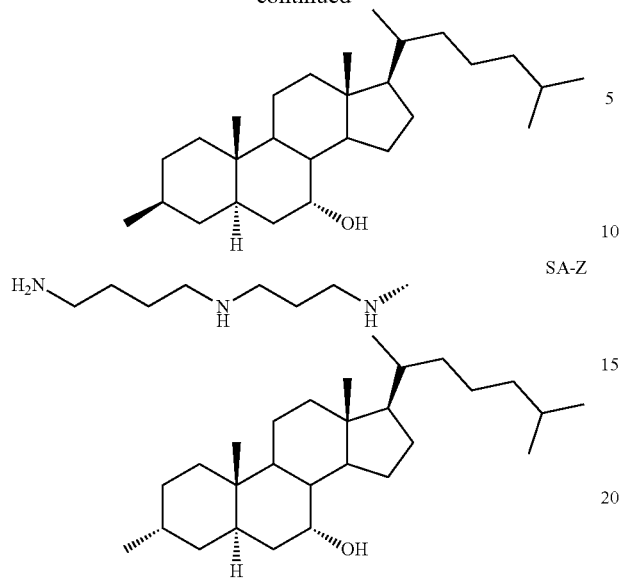

SA-Z wherein the disease is selected from the group consisting of bacterial infections, fungal infections, parasitic infections, dental infections, mastitis, metritis, pyodermatitis, and otitis.

2. The method as claimed in claim 1, in which the compounds for which p=1, q=0, m=3, n=3 or 4, and X=NH are excluded.

3. The method as claimed in claim 1, wherein:
when p=1 and q=0, then m+n≠6 or 7,
when p=0 and q=1, then m+n+o≠6 and 7.

4. The method as claimed in claim 1, in which $R_1$ is H.

5. The method as claimed in claim 1, in which X is $NR_{13}$.

6. The method as claimed in claim 1, in which $R_9$ and/or $R_{10}$ are H.

7. The method as claimed in claim 1, in which m is 2, 3, 4, or 5.

8. The method as claimed in claim 1, in which the —$NHR_2$ group is chosen from:

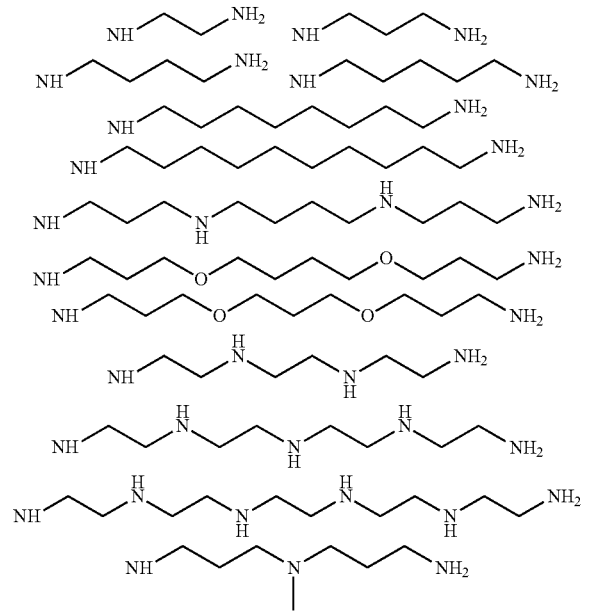

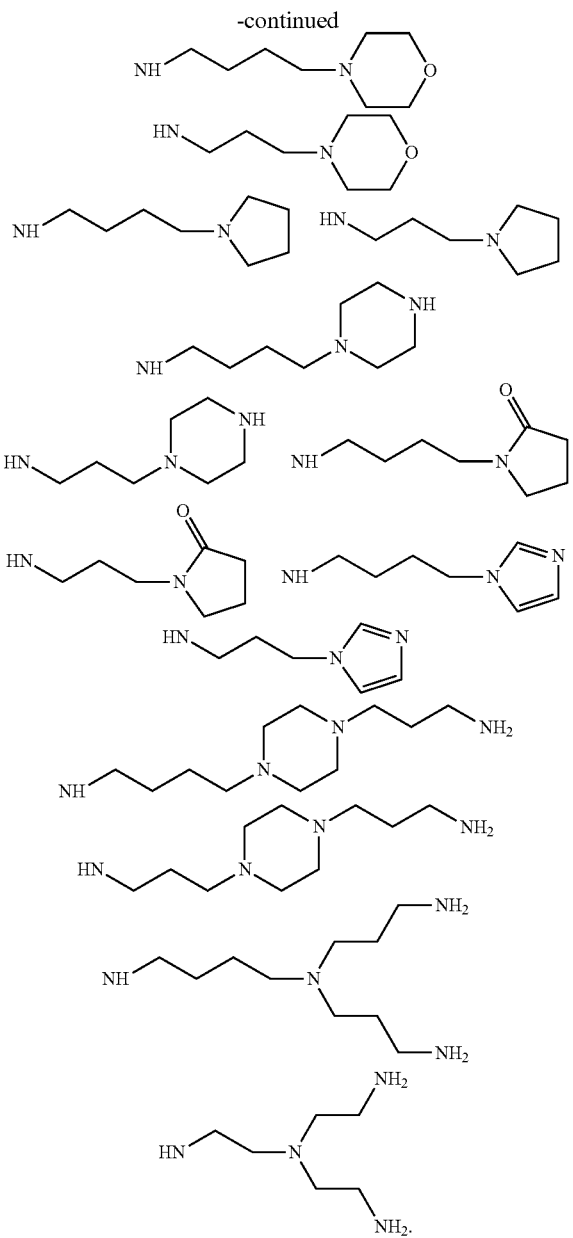

9. The method as claimed in claim 1, wherein the compound is chosen from:
3β-spermino-7α-hydroxy-5α-cholestane (SA-1)
3β-spermino-7β-hydroxy-5α-cholestane (SA-2)
3β-norspermidino-7β-hydroxy-5α-cholestane (SA-3)
3β-(1,3-diaminopropane)-7β-hydroxy-5α-cholestane (SA-4)
3β-(1,4-diaminobutane)-7β-hydroxy-5α-cholestane (SA-5)
3β-(tris(2-aminoethyl)amine)-7β-hydroxy-5α-cholestane (SA-6)
3β-(1,5-diaminopentane)-7α-hydroxy-5α-cholestane (SA-7)
3β-(1,4-bis(3-aminopropyl)piperazine)-7β-hydroxy-5α-cholestane (SA-8)
3β-(1,4-bis(3-aminopropoxy)butane)-7β-hydroxy-5α-cholestane (SA-9)
3β-(1-(3-aminopropyl)imidazole)-7α-hydroxy-5α-cholestane (SA-11)

3β-(1-(3-aminopropyl)morpholine)-7α-hydroxy-5α-cholestane (SA-12).

10. The method as claimed in claim 1, in which the bacterial infection is a Gram+ or Gram− bacterial infection.

11. The method as claimed in claim 1, wherein the animal is chosen from dogs, cats or ruminants.

12. The method as claimed in claim 1, in which the compound of formula (I) is administered in combination with an antibiotic compound.

13. The method of claim 1, wherein the human or animal is human.

* * * * *